US012588810B2

(12) United States Patent (10) Patent No.: US 12,588,810 B2

Martensen et al. (45) Date of Patent: Mar. 31, 2026

(54) ARRANGEMENT AND METHOD FOR DETERMINING EYE LENGTHS

(71) Applicant: Heidelberg Engineering Gmbh, Heidelberg (DE)

(72) Inventors: Björn Martensen, Lübeck (DE); Michaela Gaens, Dossenheim (DE); Andreas Fritz-Bouteleux, Lübeck (DE)

(73) Assignee: Heidelberg Engineering GmbH, Heidelberg (DE)

( * ) Notice: Subject to any disclaimer, the term of this patent is extended or adjusted under 35 U.S.C. 154(b) by 514 days.

(21) Appl. No.: 18/015,336

(22) PCT Filed: May 5, 2021

(86) PCT No.: PCT/EP2021/061787

§ 371 (c)(1),
(2) Date: Jan. 10, 2023

(87) PCT Pub. No.: WO2022/008116

PCT Pub. Date: Jan. 13, 2022

(65) Prior Publication Data

US 2023/0284898 A1 Sep. 14, 2023

(30) Foreign Application Priority Data

Jul. 10, 2020 (DE) ..................... 10 2020 118 331.3

(51) Int. Cl.
*A61B 3/10* (2006.01)
*A61B 3/107* (2006.01)

(52) U.S. Cl.
CPC ............ *A61B 3/107* (2013.01); *A61B 3/1005* (2013.01)

(58) Field of Classification Search
CPC .... A61B 3/00; A61B 3/10; A61B 3/12; A61B 3/14; A61B 3/102; A61B 3/103;

(Continued)

(56) References Cited

U.S. PATENT DOCUMENTS

2008/0284981 A1* 11/2008 Fercher .................. A61B 3/102
351/221
2008/0285043 A1* 11/2008 Fercher .............. G01B 9/02058
356/451

(Continued)

FOREIGN PATENT DOCUMENTS

DE 102008063225 7/2010
JP 2009-518088 5/2009

(Continued)

OTHER PUBLICATIONS

Internationaler Recherchenbericht und Schriftlicher Bescheid [International Search Report and the Written Opinion] Dated Aug. 2, 2021 From the International Searching Authority Re. Application No. PCT/EP2021/061787 and Its Translation of Search Report Into English. (13 Pages).

*Primary Examiner* — Jie Lei

(57) ABSTRACT

In view of the problem of specifying an arrangement and a method by means of which an eye can be measured preferably without artifacts and quickly, an arrangement for measuring an eye (1), comprising a light source (2) which is suitable for emitting light rays (3, 4) to the cornea (5) of an eye (1) and a control unit (6) which drives the light source (2) to emit the light rays (3, 4) and is suitable for converting reflected light rays (3a, 4a, 4b) entering the arrangement into signals (7, 8), is characterized in that the light source (2) when driven by the control unit (6) emits a central light ray (3) and emits a plurality of peripheral light rays (4) which are radially offset with respect to the central light ray (3) or in that the light source (2) when driven by the control unit (6) emits a plurality of peripheral light rays (4) radially offset with respect to one another. Moreover, a method is specified.

8 Claims, 3 Drawing Sheets

(58) Field of Classification Search
CPC ... A61B 3/0008; A61B 3/0025; A61B 3/0066;
A61B 3/117; A61B 3/1173; A61B 3/1233;
A61B 3/1241; A61B 3/107; A61B 3/1005
USPC ....... 351/206, 205, 208, 210–212, 221, 214,
351/246
See application file for complete search history.

(56) References Cited

U.S. PATENT DOCUMENTS

| | | |
|---|---|---|
| 2009/0168017 A1 | 7/2009 | O'Hara et al. |
| 2011/0069279 A1 | 3/2011 | Hacker et al. |
| 2013/0235343 A1 | 9/2013 | Hee et al. |
| 2013/0242259 A1 | 9/2013 | Hacker et al. |

FOREIGN PATENT DOCUMENTS

| | | |
|---|---|---|
| JP | 2011-509103 | 3/2011 |
| JP | 2012-513260 | 6/2012 |
| JP | 2015-509433 | 3/2015 |
| JP | 2016-028682 | 3/2016 |
| WO | WO 2007/065670 | 6/2007 |

* cited by examiner

ARRANGEMENT AND METHOD FOR DETERMINING EYE LENGTHS

RELATED APPLICATIONS

This application is a National Phase of PCT Patent Application No. PCT/EP2021/061787 having International filing date of May 5, 2021, which claims the benefit of priority of Germany Patent Application No. 10 2020 118 331.3 filed on Jul. 10, 2020. The contents of the above applications are all incorporated by reference as if fully set forth herein in their entirety.

FIELD AND BACKGROUND OF THE INVENTION

The invention relates to an arrangement and a method according to the preambles of the independent claims.

The human eye has, among other organs, the cornea, the lens, the vitreous body or corpus vitreum, the retina, the pigment epithelium, the choroid and the optic nerve. The so-called retinal pigment epithelium sets the retina off against the choroid.

To get a comprehensive picture of the dimensions of the eye, a biometry of the eye is usually performed. It is often of interest to record the length of the eyeball from the cornea to the retina, namely the so-called axial length. Usually, eye length is measured by ultrasound, time-domain OCT or low-coherence interferometry (partial-coherence interferometry), whose modes of operation can be found in the literature.

The abbreviation OCT refers to optical coherence tomography (usually abbreviated to OCT), whose mode of operation can be found in the relevant literature. Measuring an eye using so-called time-domain OCT is artifact-laden, slow and prone to false signals. With the aforementioned technologies, false signals from layers can occur, which must then be identified by a user in order to determine a correct signal from false ones. This can be automated by algorithms. The identification of artifacts and their compensation is time-consuming.

The invention is therefore based on the problem of specifying an arrangement and a method with which an eye, in particular the human eye, can be measured as quickly and free of artifacts as possible.

SUMMARY OF THE INVENTION

The present invention solves the aforementioned problem by the features of the independent claims.

Firstly, it has been recognized that a reliable signal from the retina, especially from the retinal pigment epithelium, is necessary for a measurement of eye length or other dimensions. Thereupon, it has been recognized that the signal from the retina or retinal pigment epithelium must be free of interfering influences and artifacts as well as false signals from other layers, especially the vitreoretinal interface layer. Furthermore, it has been recognized that in order to determine the eye length, a length reference of the retina to the cornea must be determined.

Against this background, it has been recognized that a plurality of light beams emitted by the light source are substantially refracted by the lens and deflected onto approximately the same point or area of the retina after these light beams have passed through the cornea at different points. According to the invention, it has then been recognized that a decentralized scanning approach is thereby possible, namely that light beams not only can be directed onto the eye along the optical axis of the eye, but also can be deflected onto the eye from being scattered around the optical axis, preferably parallel thereto. Therefore, the light source, controlled by the control unit, emits a plurality of, preferably parallel, peripheral light beams radially offset from a central light beam or from the optical axis and from one another, and creates a point pattern of light beams or light beam bundles that are incident on the cornea in off-centered fashion. The peripheral light beams can be incident on the cornea one after the other or simultaneously. It is also conceivable that the peripheral light beams are incident at the same time as the central light beam or are incident with a time-offset with respect to the latter.

This way, at least the specular reflection at the vertex of the cornea can be compensated and an associated artifact can be suppressed or compensated. The vertex is the intersection of the lens surface facing an incident light beam with the optical axis.

According to the invention, the off-centered approach to light irradiation can also compensate for or suppress artifacts that originate from deeper layers in the eye, in particular from the vitreoretinal interface layer.

The peripheral light beams, which are preferably parallel to each other, could lie within a circular area with a diameter of 3 to 12 mm, namely pass orthogonally through this circular area. This can create a point pattern on a cornea. Controlled by the control unit, the light source therefore emits the peripheral light beams and creates a point pattern on the cornea of the eye, which is scattered around the vertex of the cornea. The point pattern can be more narrowly scattered, that is to say it can also lie within a circular area with a diameter of 3 to 6 mm or of 6 to 9 mm. The size of the circle or point pattern field can be suitably chosen to make appropriate use of subapertures, since due to telecentric imaging all light beams within the point pattern field are deflected by the lens onto approximately the same point on the retina.

The control unit could automatically determine the vertex of the cornea. Alternatively or additionally, the light source, controlled by the control unit, could emit the peripheral light beams to the cornea at defined distances from the central light beam and/or at defined distances relative to one another. In this way, phase information can be obtained with adjustable resolution from the reflected light beams, especially the reflected peripheral light beams. The distances can be determined automatically by the control unit by detecting the characteristics of the cornea or by presetting possible distances.

The control unit could detect first peripheral light beams reflected by the eye, which are reflected upon incidence of the peripheral light beams and which each show different intensities, wherein the control unit detects second peripheral light beams reflected by the eye, which are reflected upon incidence of the peripheral light beams and which each show intensities which are equal or lie within a predefined interval. This allows peripheral light beams that are reflected at an interface layer between the vitreous body and the retina to be distinguished from those peripheral light beams that are reflected at the retina or the retinal pigment epithelium.

This is because peripheral light beams that are reflected at the aforementioned interface layer between the vitreous body and the retina show intensities that depend on their angles of incidence at this interface layer. The angles of incidence determine the strength of the reflection.

The intensities of peripheral light beams reflected at the retinal pigment epithelium are essentially angle invariant. The backscatter of the retinal pigment epithelium is essentially isotropic.

Against this background, the control unit could use the respective detected intensities of all reflected peripheral light beams to distinguish an organ to be detected from an organ or structure not to be detected and/or to suppress or remove an artifact from an organ or structure not to be detected. Specifically, it can be determined whether an emitted peripheral light beam was reflected by the retinal pigment epithelium or the retina, or by an interface layer between the vitreous body and retina. In this way, another artifact is able to be eliminated, in addition to the reflections at the cornea already eliminated by subapertures.

The arrangement described here could be part of an FD-OCT device, namely a Fourier domain OCT device. Such devices are also called frequency-domain OCT devices. For the purposes of this description, FD-OCT device is also understood to mean swept-source OCT devices (SS-FD-OCT devices). With the arrangement described here and the method described below, a reliable, fast and largely artifact-free determination of the eye length is possible with an FD-OCT device. The eye length can be determined using less image depth than the eye length to be measured. A reliable signal from the retina, especially the retinal pigment epithelium, is given for the measurement.

This signal is freed from interfering influences and artifacts, false signals from other layers, especially from the vitreous body/retina transition, as well as ambiguities. In FD-OCT methods, ambiguities can occur due to the Hermitian symmetry of results. When transferring from TD-OCT to FD-OCT, it must be taken into account that a signal cannot be unambiguously assigned to the Hermitian plane. This means that there are two eye lengths that match a particular signal. FD-OCT is superior to TD-OCT in terms of sensitivity, however, and so a practicably applicable solution is offered for FD-OCT by the arrangement or method described here.

Against this background, the control unit could differentiate a complex conjugate signal from a normal signal on the basis of phase information from reflected light beams, in particular from reflected peripheral light beams. Various algorithms have already become known for realizing imaging, which enable "full-range OCT" by introducing additional phase information. However, no "full-range imaging" is required as a result of the aforementioned differentiation. By differentiating the complex-conjugate signal from a normal signal on the basis of additional phase information, a length reference to the cornea can be unambiguously established.

To determine the eye length, a length reference of the retina to the cornea can be determined. The length reference can be determined by alternating between an anterior region of the eye and the retina, but this will not be discussed in detail here.

However, in order to determine the length reference independently of movement artifacts, an axial movement trajectory of two data sets is determined and taken into account for the length reference.

Advantageously, the retinal pigment epithelium is automatically detected by the arrangement and/or by the method below.

When a method for measuring an eye is carried out, light beams are transmitted to the cornea of an eye by a light source, wherein a control unit is used which controls the light source, and light beams are reflected by the eye in response to the emitted light beams and are detected and converted into signals by a control unit. A central light beam is emitted and a plurality of peripheral light beams, radially offset from the central light beam, are emitted to create a point pattern on the cornea of the eye, which is scattered around the vertex of the cornea. A plurality of peripheral light beams radially offset from one another could also be emitted to create the point pattern on the cornea of the eye, which is scattered around the vertex of the cornea.

When determining the retinal pigment epithelium, it must be ensured that the correct structure or organ is identified. One major artifact is removed or at least substantially suppressed by the off-centered scanning approach described by the method or arrangement, namely a specular reflection at an interface with the cornea. Instead of a central scan along the optical axis of the eye, the telecentric optical scan arrangement described here allows a distribution of different points outside this reflection. Nevertheless, all light beams emitted by the light source are imaged onto approximately the same point on the retina as the central light beam.

Advantageously, the points are scanned at defined distances from the vertex of the cornea, which is preferably detected automatically. Owing to the telecentric imaging, subapertures of approximately the same point are passed through, which are suggested in the literature to avoid so-called speckles.

This makes it possible to suppress a second artifact, because first peripheral light beams reflected by an interface layer between the vitreous body and the retina could be detected, which are reflected upon the incidence of the peripheral light beams and which each show different intensities depending on the angle of incidence, wherein second peripheral light beams reflected by the retinal pigment epithelium are detected, which are reflected upon the incidence of the peripheral light beams and which each show intensities which are equal or lie within a predefined interval, to be precise independently of the angle of incidence. The respective detected intensities may be used to distinguish the retina or retinal pigment epithelium from an organ or structure not to be detected and/or to suppress or remove said second artifact from the organ or structure not to be detected. The second artifact is due to a reflection at the transition from the vitreous body to the retina.

Against this background, an arrangement of the type described herein could be used to perform the method to suppress or eliminate either the first artifact and/or the second artifact. Preferably, the arrangement of the type described here is used to examine a human eye. The final diagnosis is made by a physician. The method described here is not a diagnostic method, but only provides data that a physician must finally evaluate.

In the drawing,

DESCRIPTION OF SPECIFIC EMBODIMENTS OF THE INVENTION

Figure 1:
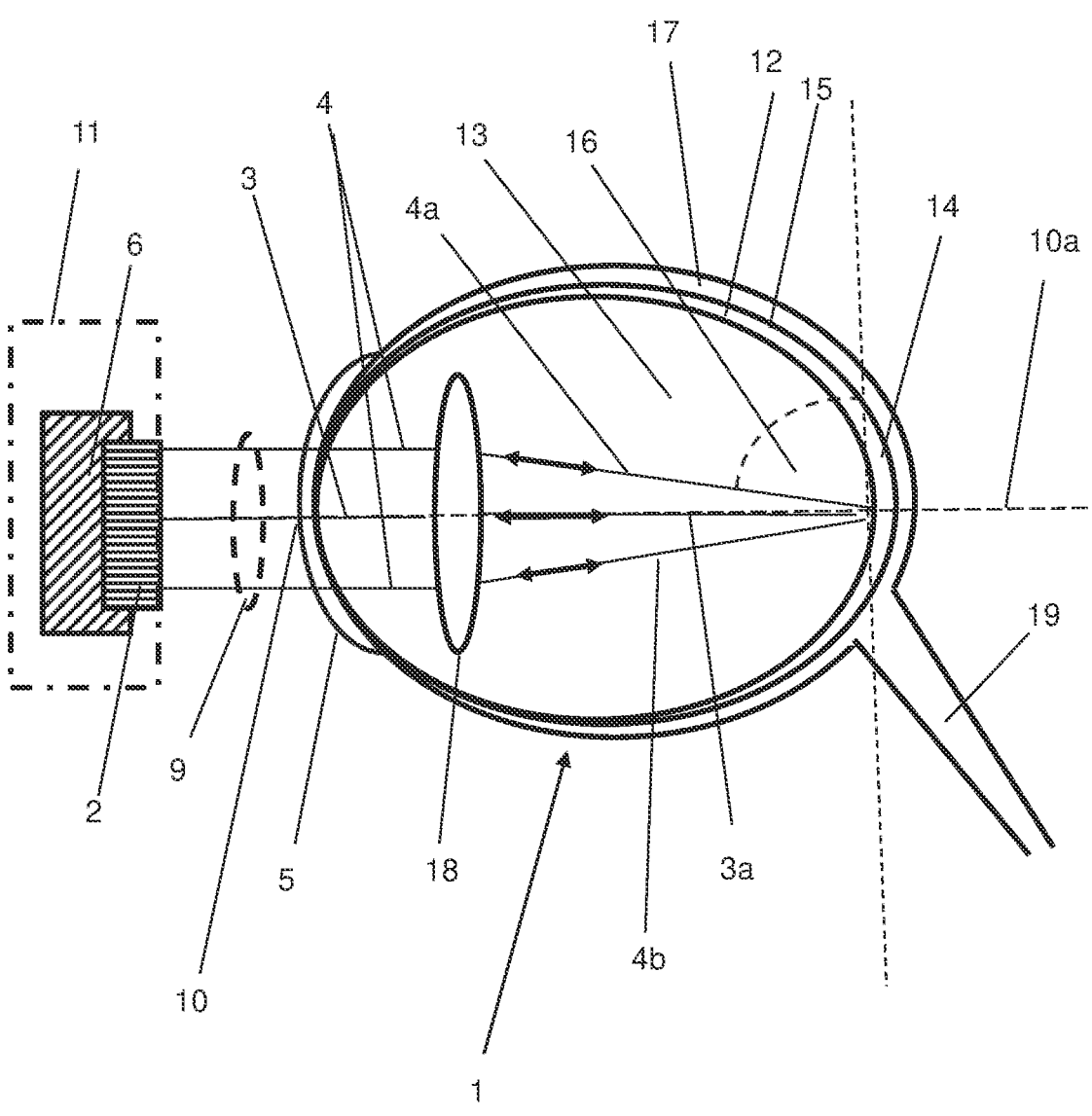
FIG. 1 shows a schematic representation of an arrangement that directs parallel light beams onto a human eye, which is shown in a sectional view.

FIG. 1 shows an arrangement for measuring a human eye 1, comprising a light source 2 which is suitable for emitting light beams 3, 4 to the cornea 5 of the human eye 1, and a control unit 6 which controls the light source 2 to emit the light beams 3, 4 and is suitable for converting reflected light beams 3a, 4a, 4b entering the arrangement into signals 7, 8 and displaying them.

Controlled by the control unit 6, the light source 2 emits a central light beam 3 and emits a plurality of peripheral light beams 4 radially offset from and parallel to the central light beam 3.

Figure 2:
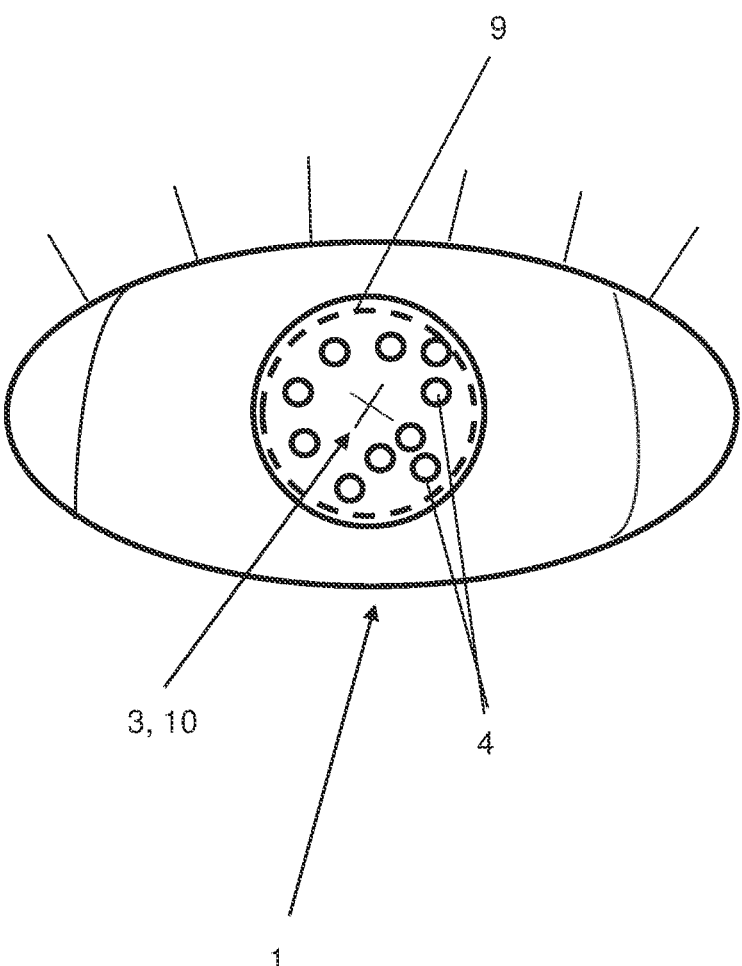
FIG. 2 shows a plan view of a human eye showing the points of incidence of parallel light beams scattered about the optical axis, thereby creating a point pattern on the cornea.

FIG. 2 shows that the peripheral light beams 4 lie within a circular area 9 with a diameter of 3 to 12 mm, namely pass orthogonally through this circular area 9. This is shown in FIG. 1 by the dashed circular area 9. The light source 2 controlled by the control unit 6 emits the peripheral light beams 4 to create a point pattern on the cornea 5 of the human eye 1, which is scattered around the vertex 10 of the cornea 5. In this respect, the control unit 6 creates the geometry of the point pattern.

The control unit 6 automatically determines the vertex 10 of the cornea 5, or its spatial position. The light source 2, controlled by the control unit 6, emits the peripheral light beams 4 to the cornea 5 at defined distances from the central light beam 3 and relative to one another.

The control unit 6 detects first peripheral light beams 4a reflected by the human eye 1, which are reflected upon the incidence of the peripheral light beams 4 and which each show different intensities. The control unit 6 also detects second peripheral light beams 4b reflected by the human eye 1, which are reflected upon the incidence of the peripheral light beams 4 and which each show intensities which are equal or lie within a predefined interval.

The control unit 6 uses the respective detected intensities to distinguish an organ to be detected from a structure not to be detected and to suppress or remove an artifact from a structure not to be detected.

The arrangement is integrated into an overarching FD-OCT device 11.

The method for measuring the human eye 1 is carried out by transmitting light beams 3, 4 to the cornea 5 of the human eye 1 by means of the light source 2, using the control unit 6 which controls the light source 2 for this purpose. Light beams 3a, 4a, 4b are reflected by the human eye 1 in response to the emitted light beams 3, 4 and are detected and converted into signals 7, 8 by the control unit 6. The reflection of the light beams 3, 4 is shown in FIG. 1 by the double-headed arrows. The reflected light beams 3a, 4a, 4b return to the control unit 6 after reflection at structures of the eye 1.

A central light beam 3 is emitted and a plurality of parallel peripheral light beams 4, radially offset from the central light beam 3, are emitted to create a point pattern on the cornea 5 of the human eye 1, which is scattered around the vertex 10 of the cornea 5.

First peripheral light beams 4a reflected by an interface layer 12 between the vitreous body 13 and the retina 14 are detected, which are reflected upon the incidence of the peripheral light beams 4 and which each show different intensities depending on the angle of incidence 16, wherein second peripheral light beams 4b reflected by the retinal pigment epithelium 15 are detected, which are reflected upon the incidence of the peripheral light beams 4 and which each show intensities which are equal or lie within a predefined interval. The intensity of these reflected second peripheral light beams 4b is independent of the angle of incidence of the incident peripheral light beams 4 associated with them.

The respective detected intensities are used to distinguish the retina 14 or retinal pigment epithelium 15 from a structure not to be detected and to suppress or remove a second artifact from the structure not to be detected.

Figure 3:
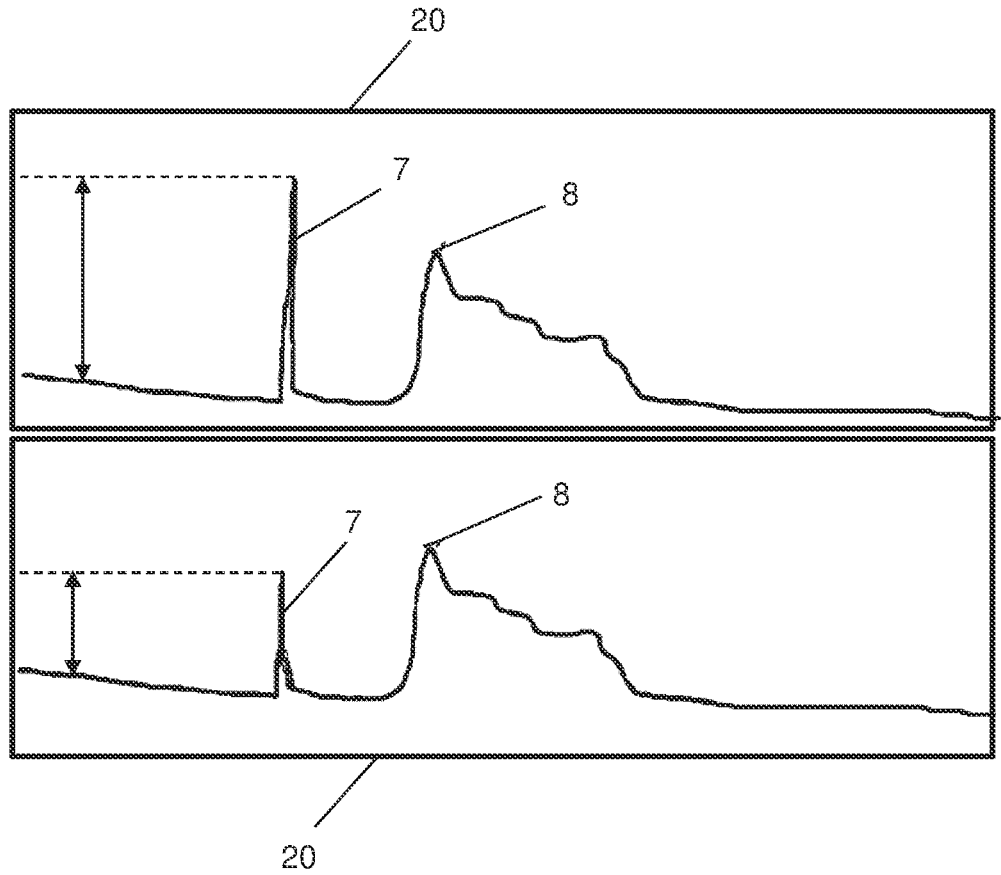
FIG. 3 shows a reduction of an artifact, wherein two signals of structures or organs are shown in comparison at different viewing angles or angles of incidence of light beams, wherein the upper signals were recorded at an almost perpendicular incidence on the vitreoretinal interface layer, and wherein the lower signals were recorded at an angle of incidence of peripheral light beams deviating greatly from 90°.

FIG. 3 shows that signals 7, 8 from the control unit 6 are shown in a display of the arrangement. In this respect, the arrangement has a display 20 for the optical representation of the signals 7, 8 of the detected organs or structures.

The display 20 shows two signals 7, 8 in each of the upper and lower view, wherein the first signal 7 comes from an artifact originating from the vitreoretinal interface layer, and the second signal 8 comes from the retinal pigment epithelium 15.

The signals 7, 8 of the upper representation of the display 20 were recorded with a light beam or light bundle incident almost perpendicularly on the vitreoretinal interface layer 12. The signals 7, 8 of the lower representation of the display 20 were detected at angles of incidence of peripheral light beams that deviate greatly from 90°.

It is clear that there is a significant reduction in the signal 7 of the artifact, namely that it is smaller than the signal 8 to be detected, which comes from the retinal pigment epithelium.

LIST OF REFERENCE SIGNS

1 Eye
2 Light source
3 Central light beam
3a Reflected central light beam
4 Peripheral light beam
4a First reflected peripheral light beam
4b Second reflected peripheral light beam
5 Cornea
6 Control unit
7 Signal from 12
8 Signal from 14 or 15
9 Circular area
10 Vertex of 1
10a Optical axis
11 FD OCT device
12 Interface layer between 13 and 14
13 Vitreous body
14 Retina
15 Retinal pigment epithelium
16 Angle of incidence
17 Choroid of 1
18 Lens of 1
19 Optic nerve
20 Display or screen of 6

The invention claimed is:
1. An arrangement for measuring an eye (1), comprising:
a light source (2) which is suitable for emitting light beams (3, 4) to the cornea (5) of an eye (1),
a control unit (6) which controls the light source (2) to emit the light beams (3, 4); and the control unit (6) is suitable for converting light beams (3a, 4a, 4b) into signals (7, 8);

wherein, the light source (2), controlled by the control unit (6), the light source emits;

a central light beam (3) and a plurality of peripheral light beams (4) radially offset from the central light beam (3);

a plurality of peripheral light beams (4) radially offset from one another;

wherein the light beams are reflected by the eye as light beams (3a, 4a, 4b) are reflected by the eye (1) in response to the emitted light beams (3, 4) and the reflected light beams are detected by the control unit; and converting the detected light beams into signals (7, 8) by the control unit (6), wherein, light beams (4a), the first peripheral light beams, are reflected by an interface layer (12) between the vitreous body (13) and the retina (14) are detected, which are reflected upon the incidence of the light beams (4) and that shows different intensities depending on the angle of incidence (16);

wherein the light beams (4b), the second peripheral light beams, reflected by the retinal pigment epithelium (15) are detected, which are reflected upon the incidence of the peripheral light beams (4) and which each show intensities which are equal or lie within a predefined interval; and wherein the respective detected intensities are used to distinguish the retina (14) or the retinal pigment epithelium (15) from an organ or structure not to be detected and/or to suppress or remove an artifact from the organ or structure not to be detected.

2. The arrangement as claimed in claim 1, characterized in that the peripheral light beams (4) lie within a circular area (9) having a diameter of 3 to 12 mm, namely pass orthogonally through this circular area (9), and/or in that the light source (2), controlled by the control unit (6), emits the peripheral light beams (4) to create a point pattern on the cornea (5) of the eye (1) which is scattered around the vertex (10) of the cornea (5).

3. The arrangement as claimed in claim 1, characterized in that the control unit (6) automatically determines the vertex (10) of the cornea (5) and/or in that the light source (2), controlled by the control unit (6), emits the peripheral light beams (4) to the cornea (5) at defined distances from the central light beam (3) and/or at defined distances relative to one another.

4. The arrangement as claimed in claim 1, characterized in that the control unit (6) uses the respective detected intensities to distinguish an organ to be detected from an organ or structure not to be detected and/or to suppress or remove an artifact from an organ or structure not to be detected.

5. The arrangement as claimed in claim 1, characterized by integration into or use with an FD-OCT device (11).

6. The arrangement as claimed in claim 1, characterized in that the control unit (6) differentiates a complex conjugate signal from a normal signal on the basis of phase information from reflected peripheral light beams (4a, 4b).

7. A method for measuring an eye (1) having a lens, cornea with a vertex, comprising:

transmitting light beams (3, 4) from a light source (2) to the cornea (5) of an eye (1);

controlling light source (2) with the control unit (6) for light beams (3, 4) from the light source;

wherein the light beams are parallel are refracted by the lens (18) of the eye (1) and deflected onto approximately the same point or area of the retina under an individual angle of incidence;

wherein the light beams are one of:

a central light beam (3) and emits a plurality of peripheral light beams (4) radially offset from the central light beam (3) configured so that a point pattern is created on the cornea (5) of the eye (1), which is scattered around the vertex (10) of the cornea (5), or a plurality of peripheral light beams (4) radially offset from one another, so that a point pattern is created on the cornea (5) of the eye (1) which is scattered around the vertex (10) of the cornea (5);

wherein the light beams are reflected by the eye as light beams (3a, 4a, 4b) are reflected by the interface layer (12) between the vitreous body (13) and the retina; the emitted light beams (3,4) are deflected onto approximately the same point or area of the retina under an individual angle of incidence (16) of the eye (1) in response to the emitted light beams (3, 4);

detecting reflected light beams by the control unit;

wherein, light beams (4a), the first peripheral light beams, are reflected by an interface layer (12) between the vitreous body (13) and the retina (14) are detected, which are reflected upon the incidence of the light beams (4) and that shows different intensities depending on the angle of incidence (16);

wherein the light beams (4b), the second peripheral light beams, reflected by the retinal pigment epithelium (15) are detected, which are reflected upon the incidence of the peripheral light beams (4) and which each show intensities which are equal or lie within a predefined interval; and the peripheral light beams are parallel, refracted by the lens (18) of the eye (1), and are deflected onto approximately the same point or area of the retina under an individual angle of incidence; and wherein the respective detected intensities are used to distinguish the retina (14) or the retinal pigment epithelium (15) from an organ or structure not to be detected and/or to suppress or remove an artifact from the organ or structure not to be detected; and converting the detected light beams into signals (7, 8) by the control unit (6).

8. The method as claimed in claim 7, wherein an arrangement for measuring the eye (1), comprising the light source (2) and the control unit (6) is used for converting the reflected light beams (3a, 4a, 4b), and for carrying out the method.

* * * * *